US007611837B2

(12) United States Patent
Yu et al.

(10) Patent No.: US 7,611,837 B2
(45) Date of Patent: Nov. 3, 2009

(54) KIT FOR DETECTING NON-PATHOGENIC OR PATHOGENIC INFLUENZA A SUBTYPE H5 VIRUS

(75) Inventors: Albert Cheung-Hoi Yu, Pok Fu Lam (CN); Ka-Lun So, Kowloon (CN); Lung-Sang Ko, Kowloon (CN); Lok-Ting Lau, Lantau (CN)

(73) Assignee: Hai Kang Life Corporation Ltd., Kowloon (HK)

( * ) Notice: Subject to any disclaimer, the term of this patent is extended or adjusted under 35 U.S.C. 154(b) by 86 days.

(21) Appl. No.: 10/398,207

(22) PCT Filed: Sep. 27, 2001

(86) PCT No.: PCT/CN01/01458

§ 371 (c)(1),
(2), (4) Date: Apr. 7, 2003

(87) PCT Pub. No.: WO02/29118

PCT Pub. Date: Apr. 11, 2002

(65) Prior Publication Data

US 2004/0142319 A1 Jul. 22, 2004

(30) Foreign Application Priority Data

Oct. 5, 2000 (CN) ................................. 00106310

(51) Int. Cl.
*C12Q 1/68* (2006.01)
*C12Q 1/70* (2006.01)

(52) U.S. Cl. ........................... 435/5; 435/6; 536/23.72; 536/24.32; 536/24.33

(58) Field of Classification Search ..................... 435/5, 435/7.1, 6; 536/23.72
See application file for complete search history.

(56) References Cited

U.S. PATENT DOCUMENTS 5,639,609 A 6/1997 Kruse-Mueller ............... 435/6
5,783,391 A 7/1998 Rossi ........................... 435/6

FOREIGN PATENT DOCUMENTS

WO WO95/20055 7/1995
WO WO96/40993 12/1996
WO WO00/17391 3/2000

OTHER PUBLICATIONS

Rahman, A. et al. Development and evaluation of NASBA and 'real-time' RT-PCR for diagnosis of viral respiratory tract infection (2000) J. Clin. Virol. 18(2000) 174 (P200).*

Horimoto et al. Direct reverse transcriptase PCR to determine virulence potential of influenza A viruses in birds (1995) J. Clin. Microbiol. 33(3), pp. 748-751.*

Collins, et al., Detection of high pathogenic and low pathogenic avian influenza subtype H5 (Eurasian lineage) using NASBA (2002) Journal of Virological Methods, vol. 103, pp. 213-225.*

Matrosovich, M. et al. The surface glycoproteins of H5 influenza viruses isolated from humans, chickens, and wild aquatic birds have distinguishable properties (1999) J. Virol. 73(2) pp. 1146-1155.*

Samuelson, A et al. Development and application of a new method for the amplification and detection of human rhinovirus RNA (1998) Journal of Virological Methods, 71:197-209.*

Romano, J.W. et al (1996) Clin. Lab. Med. 16(1):89-103.*

Starick, E. et al. Type- and Subtype-specific RT-PCR Assays for avian influenza A viruses (2000) J. Vet. Med. 47:295-301.*

Lanciotti, R.S. (2001) Journal of Clinical Microbiology, 39(12):4506-4513.*

Zhou et al, Journal of Virology, vol. 73, No. 4, pp. 3366-3374, Apr. 1999, Rapid Evolution of H5N1 Influenza Viruses in . . . .

Database EMBL EBI; XP002299292 abstract & WO00/00638A, Jan. 6, 2000, (Deursen Petrus Bernardus Hugo . . . ).

Journal of Clinical Virology 18, 2000, pp. 157-182, Molecular Diagnostics and Chip Technology.

Kwoh et al, Proc Natl Acad Sci, vol. 86, Feb. 1989, pp. 1173-1177 Transcription-based amplification system and detection of . . . .

Yuen et al, The Lancet, vol. 351, Feb. 14, 1998, pp. 467-471, Clinical Features and Rapid Viral Diagnosis of Human Disease . . . .

* cited by examiner

*Primary Examiner*—Mary E Mosher
*Assistant Examiner*—Myron G Hill
(74) *Attorney, Agent, or Firm*—Heslin Rothenberg Farley & Mesiti PC; Andrew K. Gonsalves, Esq.

(57) ABSTRACT

Current methods for detecting influenza A subtype H5 virus, for example cell culture, haemagglutination-inhibition, fluorescent antibody and enzyme immunoassay, and reverse transcriptase polymerase chain reaction (RT-PCR) may have the disadvantages of low sensitivity and low specificity. Furthermore, such methods are relatively difficult to use, and may not be suitable for routine detection on a daily basis. The kit for detecting H5 virus of this invention may provide a user-friendly alternative that is relatively more sensitive and specific to H5 virus. The detection kit utilizes two specially designed primers A and B for the replication of H5 virus, and a specific capture probe for immobilizing the amplified viral RNA. An additional primer C is also designed for the detection of pathogenic H5 virus. The detection of H5 virus by the detection kit may be accomplished within one day if desired.

14 Claims, 5 Drawing Sheets

SEQUENCE LISTING

<160> NUMBER OF SEQ IDS NOS: 14

<210> SEQ ID NO 1
<211> LENGTH: 25
<212> TYPE: DNA
<213> ORGANISM: Influenza A Subtype H5 Virus

<400> SEQUENCE: 1
tcccctgctc attgctatgg tggta                                          25

<210> SEQ ID NO 2
<211> LENGTH: 81
<212> TYPE: DNA
<213> ORGANISM: Influenza A Subtype H5 Virus

<400> SEQUENCE: 2
gtatccactc ccctgctcat tgctatggtg gtacccatac caaccatcta ccatgccctg    60
ccatcctccc tctataaaac c                                              81

<210> SEQ ID NO 3
<211> LENGTH: 120
<212> TYPE: DNA
<213> ORGANISM: Influenza A Subtype H5 Virus

<400> SEQUENCE: 3
gtggattctt tgtctgcagc gtatccactc ccctgctcat tgctatggtg gtacccatac    60
caaccatcta ccatgccctg ccatcctccc tctataaaac tgctatagct ccaaatagtc   120

<210> SEQ ID NO 4
<211> LENGTH: 31
<212> TYPE: DNA
<213> ORGANISM: Influenza A Subtype H5 Virus

<400> SEQUENCE: 4
aattctaata cgactcacta tagggagaag g                                   31

<210> SEQ ID NO 5
<211> LENGTH: 27
<212> TYPE: DNA
<213> ORGANISM: Influenza A Subtype H5 Virus

<400> SEQUENCE: 5
tgccattcca caacatacac cccctca                                        27

<210> SEQ ID NO 6
<211> LENGTH: 96
<212> TYPE: DNA
<213> ORGANISM: Influenza A Subtype H5 Virus

<400> SEQUENCE: 6
actgcaacac caagtgtcaa actccaatgg gggcgataaa ctctagtatg ccattccaca    60
acatacaccc cctcaccatc ggggaatgcc ccaaat 96

<210> SEQ ID NO 7
<211> LENGTH: 136
<212> TYPE: DNA
<213> ORGANISM: Influenza A Subtype H5 Virus

```
<400> SEQUENCE: 7
aagtgaattg gaatatggta actgcaacac caagtgtcaa actccaatgg gggcgataaa    60
ctctagtatg ccattccaca acatacaccc cctcaccatc ggggaatgcc ccaaatatgt   120
gaaatcaaac agatta                                                   136

<210> SEQ ID NO 8
<211> LENGTH: 20
<212> TYPE: DNA
<213> ORGANISM: Influenza A Subtype H5 Virus

<400> SEQUENCE: 8
gatgcaaggt cgcatatgag                                                20

<210> SEQ ID NO 9
<211> LENGTH: 25
<212> TYPE: DNA
<213> ORGANISM: Influenza A Subtype H5 Virus

<400> SEQUENCE: 9
gagagaagaa gaaaaaagag aggac                                          25

<210> SEQ ID NO 10
<211> LENGTH: 94
<212> TYPE: DNA
<213> ORGANISM: Influenza A Subtype H5 Virus

<400> SEQUENCE: 10
tcaaacagat tagttcttgc gactggactc agaaataccc ctcaaaggga gagaagaaga    60 aaaagagag gactatttgg agctatagca ggtt                                 94

<210> SEQ ID NO 11
<211> LENGTH: 134
<212> TYPE: DNA
<213> ORGANISM: Influenza A Subtype H5 Virus

<400> SEQUENCE: 11
aatgccccaa atatgtgaaa tcaaacagat tagttcttgc gactggactc agaaataccc    60
ctcaaaggga gagaagaaga aaaagagag gactatttgg agctatagca ggttttatag   120
agggaggatg gcag                                                     134

<210> SEQ ID NO 12
<211> LENGTH: 22
<212> TYPE: DNA
<213> ORGANISM: Influenza A Subtype H5 Virus

<400> SEQUENCE: 12
ctatttggag ctatagcagg tt                                             22

<210> SEQ ID NO 13
<211> LENGTH: 91
<212> TYPE: DNA
<213> ORGANISM: Influenza A Subtype H5 Virus

<400> SEQUENCE: 13
ggactcagaa ataccctca aagggagaga agaagaaaaa agagaggact atttggagct    60
atagcaggtt ttatagaggg aggatggcag g                                   91
```

-continued

```
<210> SEQ ID NO 14
<211> LENGTH: 131
<212> TYPE: DNA
<213> ORGANISM: Influenza A Subtype H5 Virus

<400> SEQUENCE: 14
acagattagt tcttgcgact ggactcagaa atacccctca aagggagaga agaagaaaaa      60
agagaggact atttggagct atagcaggtt ttatagaggg aggatggcag ggcatggtag     120
atggttggta t                                                          131
```

KIT FOR DETECTING NON-PATHOGENIC OR PATHOGENIC INFLUENZA A SUBTYPE H5 VIRUS

This is a nationalization of PCT/CN01/01458, filed Sep. 27, 2001 and published in English.

FIELD OF THE INVENTION

This invention relates to apparatus for detecting influenza A subtype H5 virus.

BACKGROUND OF TH INVENTION

Avian influenza (Influenza A) viruses infect a variety of animals, including humans, pigs, horses, sea mammals, and birds. Recent phylogenetic studies of Influenza A viruses have revealed species-specific lineages of viral genes and have demonstrated that the prevalence of interspecies transmission depends on the animal species They have also revealed that aquatic birds are the source of all influenza viruses in other species.

The emergence of a "new" Influenza A virus in humans is possible. Serological and virological evidence suggests that since 1889 there have been six instances of the introduction of an influenza virus with an HA subtype that had been absent from human population for some time. Three human subtypes of HA have appeared cyclically—subtype H2 in 1889, H3 in 1900, H1 in 1918, H2 again in 1957, H3 again in 1968, and H1 again in 1977. The first human infection with avian influenza A subtype H5N1 was reported in 1997, which resulted in the death of a 3-year-old boy. This first report leads to the need for the routine screening for H5 virus in animals, particularly chicken, in stopping the spread of the viruses.

Many methods for viral identification are currently being used, including cell culture, haemagglutination-inhibition, fluorescent antibody and enzyme immunoassay, and reverse transcriptase polymerase chain reaction (RT-PCR). However, these methods all share the same problems—they have relatively low sensitivity and low specificity. Furthermore, the detection time may be too long for routine detection purposes, and such methods are relatively difficult to be utilized.

The current methodologies applied for detecting influenza A subtype H5 virus includes immunodiagnostic assay and virus culture. Examples of immunodiagnostic essay include haemagglutinin inhibition (HI) assay and immuno assay. However, immunodiagnostic assay may have the disadvantage of low sensitivity. Furthermore, as the target of immunodiagnostic assay is usually a specific protein, the underlying genetic nature of a target may not be obtained directly. In addition, the initial derivation of antibodies is ultimately dependent upon the antigenicity of the protein analysis in the immune host animal and therefore, cross-reactivity may occur.

Although virus culture is an accurate and low cost detection method, it is relatively labour intensive and requires a lot of space for incubation. The culturing process may be slow and cannot meet the demand of daily inspection. In addition, virus culture can not provide the detection results directly and has to reply upon further confirmation by other detection methods, which may be very expensive.

OBJECT FOR THE INVENTION

Therefore, it is an object of this invention to design a user-friendly diagnostic kit for detecting H5 virus such that the sensitivity and specificity may be improved.

Another object of this invention to design a kit for detecting influenza A subtype H5 virus such that the detection time and the overall costs for detection may be reduced.

It is yet another object of this invention to design a kit for detecting influenza A subtype H5 virus such that the pathogenicity of the H5 virus may be detected directly.

As a minimum, it is an object of the present invention to provide the public with a useful choice.

SUMMARY OF THE INVENTION

Accordingly, this invention provides a kit for detecting non-pathogenic or pathogenic influenza A subtype H5 virus in a biological sample including:
  an isolating agent for isolating the RNA molecules of H5 virus from the biological sample;
  a nucleic acid replicating agent for replicating a target molecule, wherein the target molecule includes:
    a nucleic acid sequence complementary to at least a portion of the RNA sequence of H5 virus and
    a nucleic acid sequence for binding to a detection molecule;
  a nucleic acid detecting agent for detecting the target molecule, wherein the nucleic acid detecting agent includes the detection molecule.

It is another aspect of this invention to provide a purified and isolated DNA molecule or the complementary DNA molecule including:
  a first DNA sequence for binding to at least a portion of the RNA sequence of influenza A subtype H5 virus; and
  a second DNA sequence encoding a promoter DNA sequence of a RNA polymerase such that the purified and isolated DNA molecule extends in the presence of an enzyme and DNA nucleotides to generate a DNA sequence including:
  a DNA sequence complementary to at least a portion of the RNA sequence of H5 virus, and
  a DNA sequence encoding the promoter DNA sequence of a RNA polymerase
when the first purified and isolated DNA molecule binds to at least a portion of the RNA sequence of H5 virus.

It is yet another aspect of this invention to provide a purified and isolated DNA molecule or the complementary DNA molecule including:
  a first DNA sequence encoding at least a portion of the RNA sequence of non-pathogenic or pathogenic influenza A subtype H5 virus, and
  a second DNA sequence encoding a DNA sequence for binding to a detection molecule such that the purified and isolated DNA molecule extends in the presence of an enzyme and DNA nucleotides to generate a DNA sequence including:
  a DNA sequence encoding at least a portion of the RNA sequence of non-pathogenic or pathogenic influenza A subtype H5 virus; and
  a DNA sequence encoding the DNA sequence for binding a detection molecule
when the purified and isolated DNA molecule binds to a DNA molecule including a DNA sequence complementary to at least a portion of the RNA sequence of non-pathogenic or pathogenic H5 virus.

This invention also provides a purified and isolated DNA molecule or the complementary DNA molecule consisting of a first DNA sequence encoding either one of the DNA sequences set forth in SEQ ID No.5, 6, 7, 9, 10, or 11.

It is yet another aspect of this invention to provide a purified and isolated DNA molecule or the complementary DNA molecule including:
   a first DNA sequence encoding at least a portion of the RNA sequence of influenza A subtype H5 virus for binding to a target molecule, wherein the target molecule includes a nucleic acid sequence complementary to at least a portion of the RNA sequence of influenza A subtype H5 virus; and
   an immoblizer
such that the target molecule is immoblized when bound to the purified and isolated DNA molecule.

It is another aspect of this invention to provide a purified and isolated DNA molecule or the complementary DNA molecule including:
   a first DNA sequence encoding at least a portion of the RNA sequence of influenza A subtype H5 virus for binding to a target molecule, wherein the target molecule includes a nucleic acid sequence complementary to at least a portion of the RNA sequence of influenza A subtype H5 virus; and
   a signal generator
such that a signal is generated from the target molecule when the target molecule is bound to the purified and isolated DNA molecule.

This invention also provides the use of a first and a second purified and isolated DNA molecules in the manufacture of a kit for the detection of influenza A subtype H5 virus in a biological sample, wherein:
   the RNA molecule of H5 virus is isolated from the biological sample by an isolating agent,
   a target molecule is replicated by a nucleic acid replicating agent including the first and the second purified and isolated DNA molecules, wherein the target molecule includes:
      a nucleic acid sequence complementary to at least a portion of the RNA sequence of H5 virus; and
      a nucleic acid sequence for binding to a detection molecule;
   the target molecule is detected by a nucleic acid detecting agent, wherein the nucleic acid detecting agent includes the detection molecule.

BRIEF DESCRIPTION OF THE DRAWINGS

A preferred embodiment of this invention will now be described with reference to the following figures.

Figure 1:
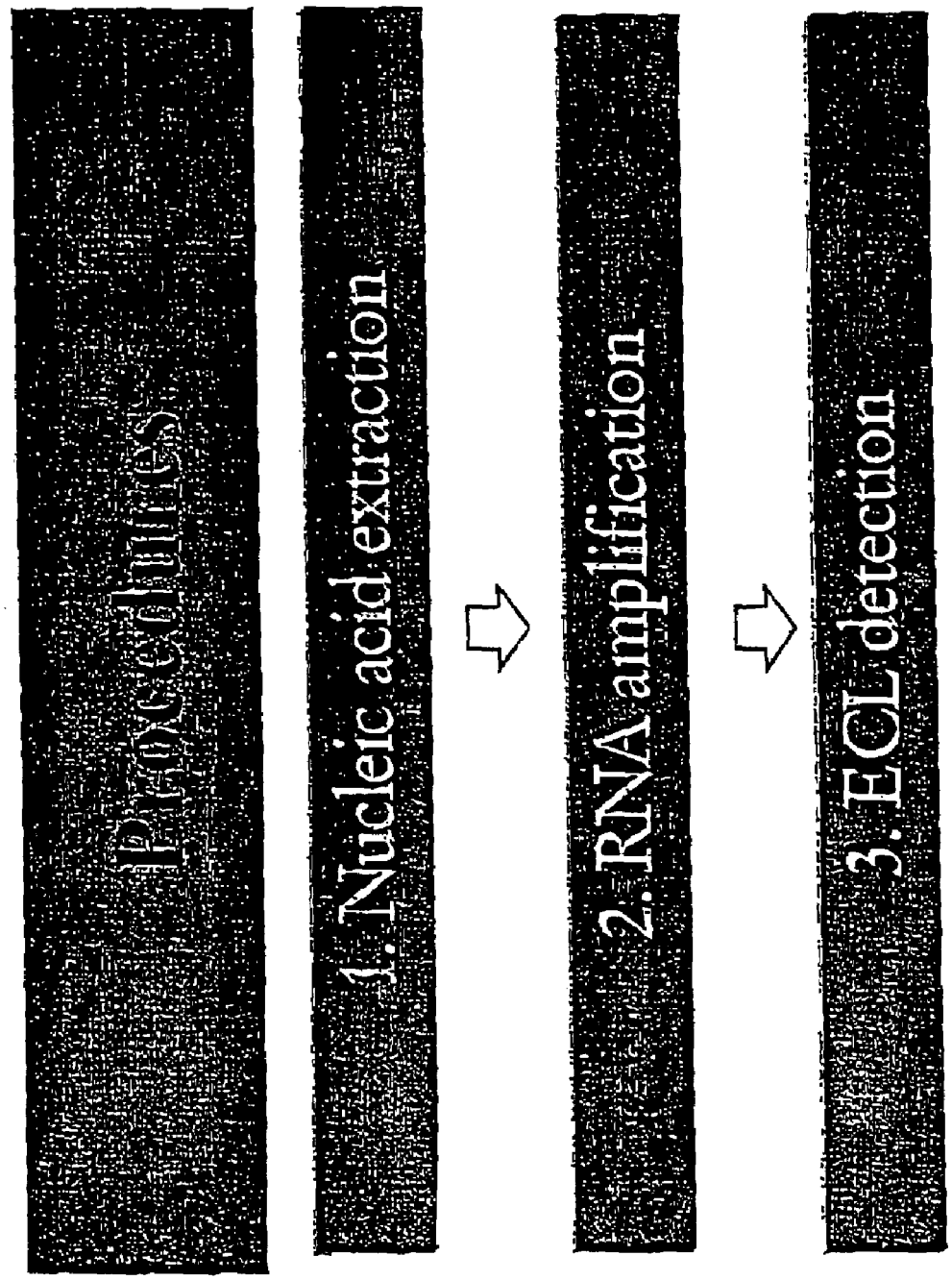
FIG. 1 shows the flow chart of the overall procedures of the detection of influenza A subtype H5 virus by the kit of this invention.

SEQ ID Nos. 1-14 show the nucleic acid sequences for this invention, respectively, which are used in the DNA molecules of the detection kit for amplification and detection purposes.

DETAILED DESCRIPTION OF PREFERRED EMBODIMENTS

Preferred embodiments of this invention are now described with reference to the figures. List 1 is a part list so that the reference numerals in the figures may be easily referred to.

The concentration of influenza A subtype H5 in a biological sample, for example chicken blood, may be very low such that detection of the presence of R viral RNA may not be performed on the biological sample directly. In order to increase the number of the viral RNA molecules to a sufficient amount for the detection purpose, a suitable amplification technology is required. Nucleic acid sequence-based amplification (NASBA) is known to be a flexible technology with particular use for the amplification of RNA. The amplified RNA molecules may then be detected by suitable technology. NASBA is a rapid, highly sensitive and highly specific method for the detection of influenza virus subtype I-5. Results can be obtained in as little as one day. In addition, it can discriminate between pathogenic and non-pathogenic H5 strains directly.

Influenza virus contains its genetic material in the form of a single strand of viral ribonucleic acid (RNA). Influenza A subtype H5 viral RNA contains the genes necessary for its reproduction and one of the essential genes is called haemagglutinin. This gene is approximately 1756 nucleotides in length, and the nucleotides are numbered from the 5' end of the molecule.

FIG. 1 shows the overall procedures for the detection of H15 virus by the detection kit. As shown in FIG. 1, the target H5 viral nucleic acid molecule, which is in, the form of a single strand of RNA molecule, is firstly extracted from a biological sample. The compatible biological sample types may include blood, serum/plasma, peripheral blood mononuclear cells/peripheral blood lymphocytes (PBMC/PBL), sputum, urine, faeces, throat swabs, dermal lesion swabs, cerebrospinal fluids, cervical smears, pus samples, food matrices, and tissues from various parts of the body including brain, spleen, and liver. Other samples that have not been listed may also be applicable. The nucleic acid extraction process of the detection kit of this invention is accomplished by an isolating agent.

After the target H5 viral RNA molecule is extracted from the biological sample, the amount of RNA molecules in the sample may not be sufficient to be detected. Therefore, a portion of the H5 viral RNA molecule is replicated to a target nucleic acid molecule by an appropriate amplification technique, for example, NASBA. The target nucleic acid molecules may then be detected by suitable methods.

After the overall procedures of the detection kit of the invention described, the details of each procedure will now be discussed.

Figure 2:
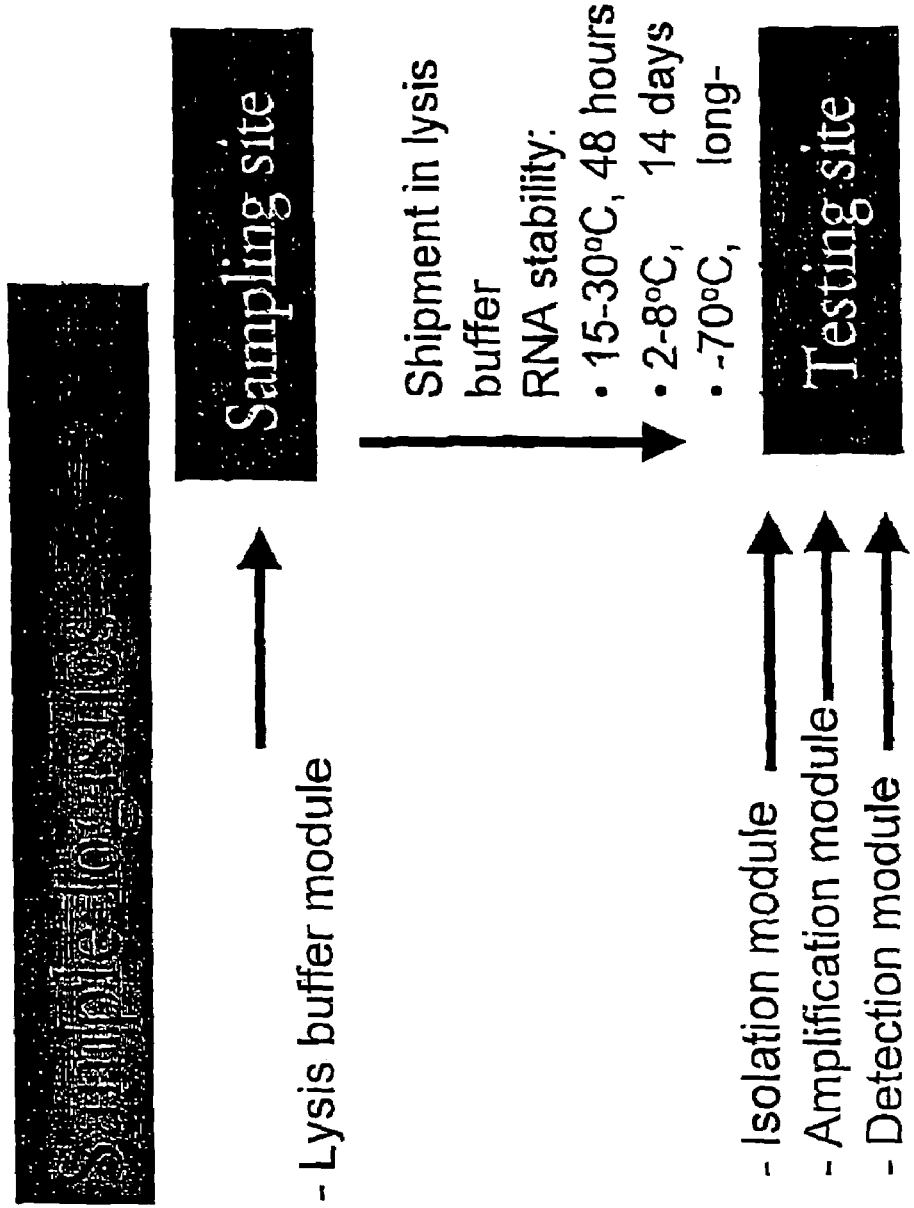
FIG. 2 shows fee detailed procedures for the detection of influenza A subtype H5 virus by the detection kit of this invention.

The H5 viral RNA molecule may be isolated from the biological sample by applying a suitable isolating agent to the biological sample. Preferably, a lysis agent may be applied before the isolating agent. The lysis agent, for example, a lysis buffer, is responsible for dissolving the proteins and lipids, and denaturing the proteins in the biological sample such that these materials may be removed from the sample more easily. Furthermore, the lysis agent may also serve as a buffer for stablizing the RNA molecule for long term storage purposes. As shown in FIG. 2, the RNA molecule may be stable in the lysis buffer for up to 48 hours at room temperature and may be stored indefinitely at −70° C. The advantages for doing so is that it may not be necessary to perform the analysis at the sampling site, which may not be suitable for carrying out such processes.

An example of suitable lysis buffer may include 5M guanidine thiocyanate and Tris/HCl. The lysis buffer forms no invention of the detection kit and the compositions suitable for its purpose are well known to the art. Therefore, the detailed composition of the lysis buffer will not be discussed here. Lysis agents hating different compositions that can still achieve the purposes of dissolving proteins and lipids, denaturing proteins, and stablizing the RNA molecules may be utilized in the detection kit of this invention.

Figure 3:
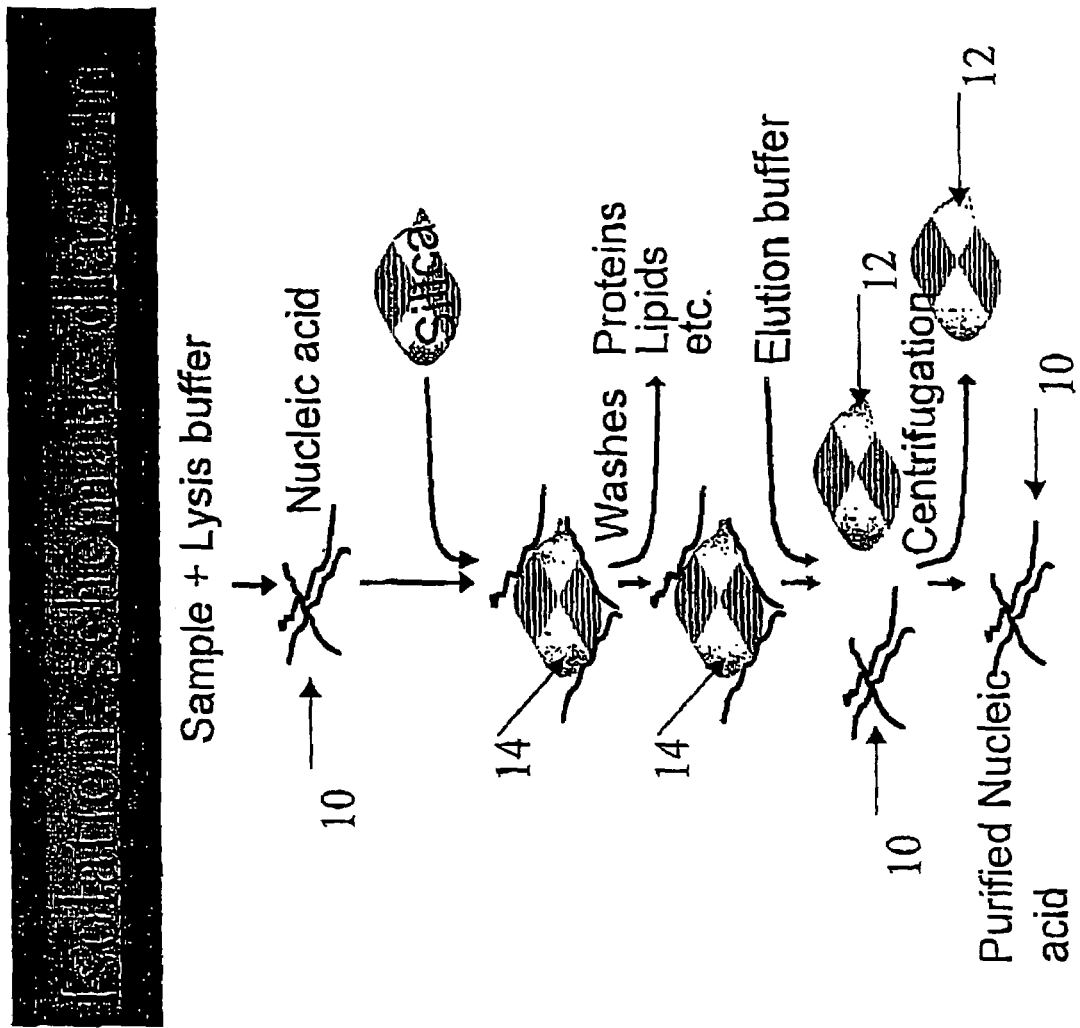
FIG. 3 shows the isolation of the viral RNA molecules from the biological sample.

After the lysis agent has been applied to the biological sample, the next step is the isolation of the nucleic acid molecules from the sample through the use of an isolating agent. FIG. 3 describes the overall isolation procedure in the detection kit After the lysis agent is applied to the biological sample, nucleic acids (10) together with other unwanted components are in the form of a solution. An adsorbent, for example silica (12), may then be added into the solution to adsorb the nucleic acids (10), resulting in a nucleic acids/silica mixture (14). After that, proteins and lipid and other unwanted materials in the solution may be washed away by suitable eluents, for example, 5M guanidine thiocyanate and Tris/HCl solution, Tris/HCL solution, 70% ethanol, or acetone, or their combinations. After the mixture (14) is washed with sufficient amount of eluents, the nucleic acids (10) in the silica (12) may then be isolated by centrifugation.

After the nucleic acids (12) contained in the sample are isolated, an amplification agent may then be applied to the mixture of nucleic acid such that the H5 viral RNA molecule is replicated for detection purposes, for example NASBA technique. Three purified and isolated DNA molecules are designed for the amplification purpose, which are termed primers A to C.

Figure 4:
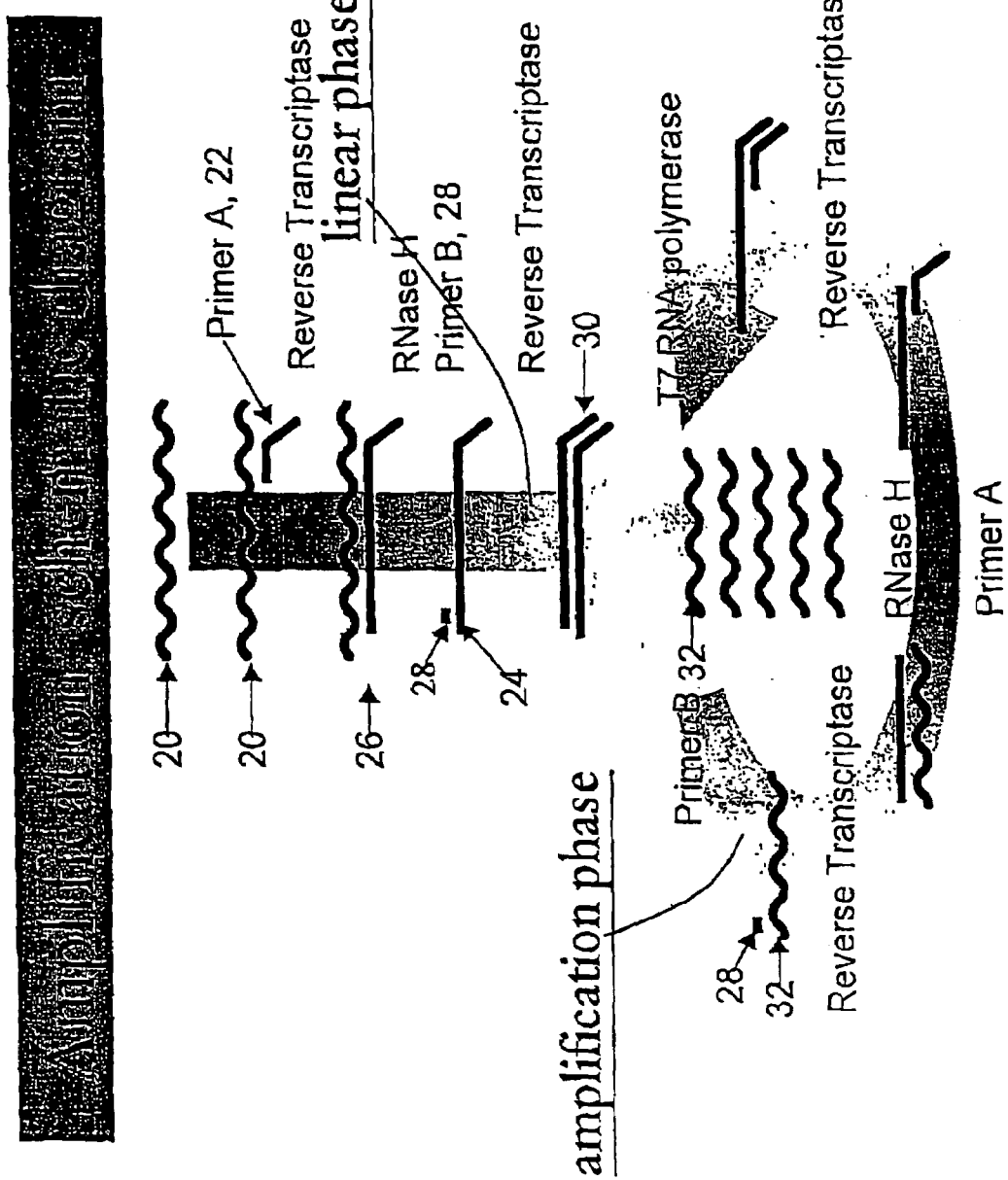
FIG. 4 shows the amplification of a portion of the influenza A subtype H5 viral RNA molecule by two DNA molecules, primers A and B.

FIG. 4 shows a schematic diagram for the amplification of the H5 viral RNA by NASBA in this invention. As shown in the figure, the amplification process is initiated by the annealing of primer A (22) to the target H5 viral RNA (20), which is a single-stranded RNA molecule. The primer A (22) is designed such that it is capable of binding to the targeted RNA molecule, and further includes a DNA sequence encoding the promoter for a RNA polymerase, preferably bacteriophage T7 RNA polymerase. The precise location of binding depends upon the strain of virus examined. The binding site may change after a certain period of time. The important technical feature of Primer A is that it remains capable of binding to a portion of H5 virus.

Accordingly, primer A (22) includes a binding sequence encoding a DNA sequence complementary to at least a portion of the H5 viral RNA (20). For the purpose of this invention, it is found that the region suitable for binding in the H5 viral RNA (20) is a region between nucleotides 1107 to 1132 of the haemagglutinin gene of H5 virus, which is found to contain the least number of nucleotides for the binding function. Therefore, the binding sequence of Primer A preferably includes a DNA sequence that is complementary to region between nucleotide 1107 to 1132 of the haemagglutinin gene of H5 virus, which is set forth in SEQ ID No. 1. It should be noted that SEQ ID No. 1 is formally written in the 5'-3' direction. As a result the orientation of binding with respect to the viral gene is from "back" to "front".

As an alternative, nucleotides 1060 to 1140 (SEQ ID No.2) or nucleotides 1040 to 1160 (SEQ ID No.3) of the haemagglutinin gene of H5 virus may be used for the binding purpose in primer A (22).

For the amplification purpose, which will be described in more detail in the specification, primer A (22) further includes a DNA sequence encoding a promoter of a RNA polymerase, for example bacteriophage T7 RNA polymerase. A suitable promoter DNA sequence is set forth in SEQ ID No.4). The promoter sequence is preferably attached to the 5' end of the binding sequence, such that the binding sequence may extend at the 3' end when Primer A binds to H5 viral RNA. If other RNA polymerase is utilized, the promoter sequence will have to be changed accordingly.

After the primer A binds to the H5 viral RNA, the primer A is extended through the action of a suitable reverse transcriptase, for example Avian Myoblastosis Virus-Reverse Transcriptase (AMV-RT) in the presence of suitable nucleotides at the 3' end of Primer A. Therefore, an extended Primer A (24) including the following sequences is resulted:
  (a) a DNA sequence that is complementary to a portion of H5 viral RNA; and
  (b) a DNA sequence encoding a promoter for a RNA polymerase.

The H5 RNA portion of the resulting DNA:RNA hybrid (26) is eliminated through the action of RNase H. This allows for the primer B (28) to anneal to the extended Primer A (24) at a position that is upstream from the primer A (22) annealing site. Therefore, in order for the primer B (28) to bind to the extended Primer A (24), primer B (28) includes a first binding DNA sequence encoding a portion of the H5 viral haemagglutinin gene sequence. Preferably, this first DNA sequence of primer B (28) encodes nucleotides 914 to 940 of the haemagglutinin gene of H5 virus (SEQ ID No.5). As an alternative, nucleotides 866 to 961 (SEQ ID No.6) or Nucleotides 846 to 981 (SEQ ID No.7) of H5 viral haemagglutinin gene may be utilized.

To achieve the detection purpose, primer B (28) may father include a second DNA sequence that is complementary to the nucleic acid sequence of a detection molecule. If the detection molecule is designed in a way such that it includes a DNA sequence encoding a portion of the RNA sequence of H5 virus such that it may bind to the amplified RNA molecules, it may not be necessary for primer B to include the second DNA sequence. In this case, primer B may consist of merely the first DNA sequence.

As an alternative, a second DNA sequence encoding the DNA sequence set forth in SEQ ID No.8 is included in Primer B. The second DNA sequence is preferably attached to the 5' end of the binding sequence of Primer B. SEQ ID No. 8 is subjected to change if other detection nucleic acid sequences are used.

After the annealing of primer B (28) to the extended Primer A (24), primer B (28) extends dot through the T7 RNA ploymerase promoter at the end of the extended primer A (24) through the action of AMV-RT. As a result, a double-stranded DNA copy (30) of the original H5 viral RNA target sequence is produced, encoding all intact T7 RNA polymerase promoter at one end and a portion of H5 viral RNA sequence at the other end. This promoter is then recognized by the T7 RNA polymerase, resulting in the production of large amount of target RNA molecules (32) that include a RNA sequence complementary to a portion of the original H5 viral RNA sequence.

Primer B may be used to determine non-pathogenic strains of influenza. A subtype H5 virus. For the detection of the pathogenic H5 virus, a primer C is used in place of primer B. Again primer C is a purified and isolated DNA molecule including the following DNA sequences:
  a first DNA sequence encoding at least a portion of the RNA sequence of pathogenic H5 virus; and
  a second DNA sequence encoding a DNA sequence complementary to a detection DNA sequence. As in the case of Primer B, this second DNA sequence may be a purely optional component.

The function and working of Primer C is the same as Primer B, except that the target is pathogenic H5 virus.

Preferably, the first DNA sequence of primer C encodes nucleotide 1017 to 1042 of the haemagglutinin gene of H5 virus (SEQ ID No.9). As an alternative, nucleotide 970 to 1063 (SEQ ID No.10) or nucleotide 950 to 1083 (SEQ ID No.11) of H5 viral haemagglutinin gene may be utilized.

It is found that Primer C does not replicate the target H5 viral RNA efficiently from freshly isolated nucleic acids from the samples with Primer A (22). Therefore, it is preferred that Primer C is applied to amplified RNA from samples testing positive for H5 virus using Primers A (22) and B (28).

The product of the amplification process is a large quantity of target RNA molecules (32) each containing the following RNA sequences:
(a) a RNA sequence complementary to a portion of the original H5 viral RNA (pathogenic or non-pathogenic); and
(b) a RNA sequence complementary to the nucleic acid sequence of a detection molecule, if Primer B or C includes the corresponding second DNA sequence.

The target RNA molecule (32) of this particular embodiment filer includes a RNA sequence encoding the promoter for T7 RNA polymerase, which is automatically included during the amplification process by the T7 RNA polymerase. However, this segment of RNA sequence may have no function in the detection step.

Figure 5:
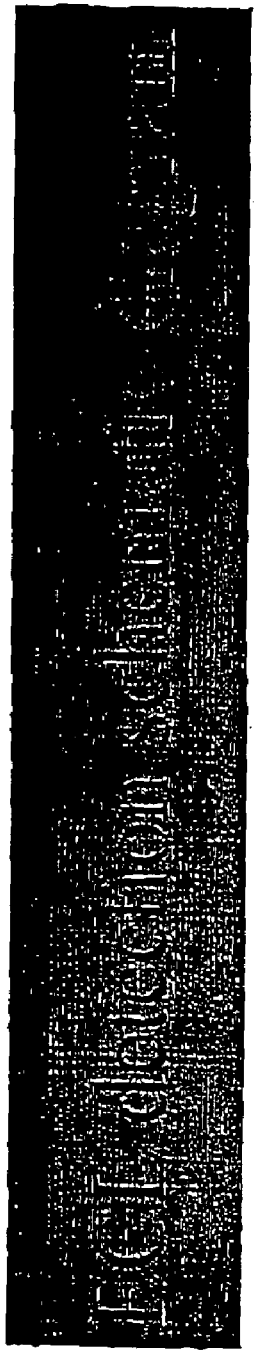
FIG. 5 shows the immobilization of the amplified RNA molecule while bound to a detection probe.
Figure 5:
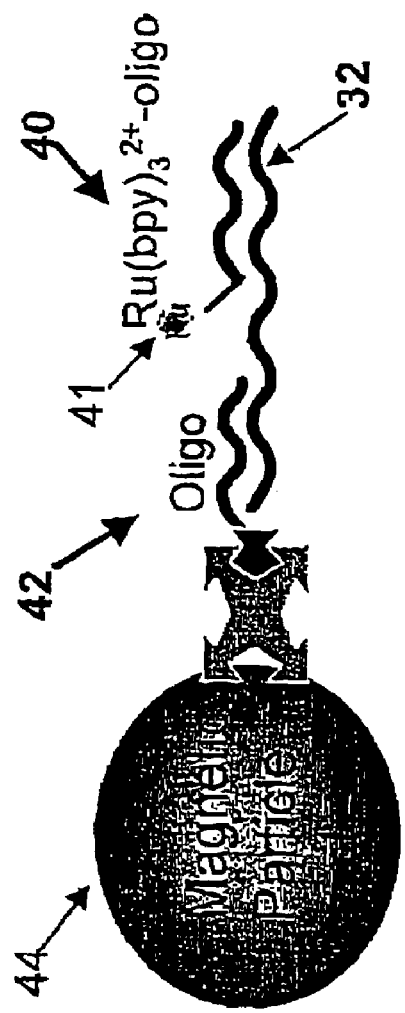
Figure 5:

The detection of the target RNA molecule (32) is illustrated in FIG. 5. The target RNA molecule (32) may be detected by binding to the detection molecule that is capable of generating a signal, for example the detection probe (40). The signal may be generated from a signal generator (41) that is attached to the detection probe (40). In this particular preferred embodiment as shown in FIG. 5, the signal generator (41) is a ruthenium-bipyridine complex $[Ru(bpy)_3]^{2+}$. As an alternative, the signal generator (41) may be radioactive (e.g. $^{32}P$), chemiluminescent (e.g. luciferin/luciferase) fluorescent (e.g. fluorescein), enzymatic (e.g. alkaline phosphatase, horseradish peroxidase), or other electrochemiluminescence molecules.

If primers B or C includes the corresponding second DNA sequence that is complementary to a detection DNA sequence, the target RNA molecule (32) includes a RNA sequence complementary to the nucleic acid sequence of the detection molecule. The advantage of utilizing such a design is that commercially available detection molecules may be used.

If primers B or C consists of merely the first DNA sequence that encodes a portion of the H5 viral haemagglutinin gene sequence, a new detection molecule is required. In this case, the detection molecule may include:
a nucleic acid sequence encoding a portion of H5 viral RNA sequence that is complementary to that encoded in the target RNA molecule (32); and
a signal generator.

The target RNA molecule (32) is contained in a mixture together with other undesired components including the unamplified nucleic acids contained in the original sample, the primers A, B, and C, the unreacted nucleotides, and most importantly, the unbound detection molecules. Therefore, the target RNA molecule (32) may be immoblized by a capture molecule, for example the capture probe (42), such that the undesired components may be washed away. The capture probe (42) is capable of binding to the target RNA molecule (32). This may be achieved by including a nucleic acid sequence encoding a portion of H5 viral RNA sequence that is complementary to that encoded in the target RNA molecule (32). The capture probe (42) is further attached to an immobilizer (44), which may immobilize the target RNA molecule (32) so that other undesired components may be washed away. The immobilizer (44) as shown in FIG. 5 is a magnetic particle that may be attracted to a working electrode. Other immobilizers may also be utilized, for example, a piece of polymer wit a number of capture probes (42) attached on.

The sequence of the detection probe may be complementary to any region of the amplified RNA product whose ends are defined by primers A and B or by primers A and C. However, the detection probe sequence cannot overlap that of the capture probe, as this would affect the interaction of the amplified RNA with the capture probe and vice versa.

As shown in FIG. 5, the target RNA molecule may be immobilized together with the detection probe (40). Therefore, there may be no restriction on the timing of the addition of the capture probe (42) into the mixture. The capture probe (42) may be added after or before the addition of the detection probe (40), as long as the capture probe is added before the washing step.

As the nucleic acid sequences of Primers A, B, and C, and the capture probe are now known, the synthesis of the corresponding complementary DNA molecules will be apparent to one skilled in the art. Such complementary DNA molecules may be used as templates in the synthesis of Primers A, B, and C, and the capture probe.

The present invention is now illustrated by the following non-limiting examples. It should be noted that various changes and modifications can be applied to the following example and processes without departing from the scope of this invention. Therefore, it should be noted that the following example should be interpreted as illustrative only and not limiting in any sense.

EXAMPLE

The detailed components of the detection kit of this example are listed as follows:

A. Lysis Buffer

50×0.9 ml Lysis buffer (5M guanidine thiocynante, Triton X-100, Tris/HCl)

B. Nucleic Acid Isolation Components

5×22 ml Wash Buffer (5M guanidine thiocyanate, Tris/HCl)
5×0.8 ml Silica (Hydrochloric acid-activated silicon dioxide particles)
5×1.5 ml Elution buffer (Tris/HCl)

C. Nucleic Acid Amplification Components

5×60 µl Enzyme solution (Avian Myoblastosis Virus-Reverse Transcriptase (AMV-RT), RNase-H, T7 RNA polymerase stabilized with bovine serum albumin)
5×10 mg Reagent spheres (lyophilised spheres with nucleotides, dithiothreitol and $MgCl_2$). Contained in a foil pack with silica gel desiccant
1×0.6 ml Reagent sphere diluent (Tris-HCl, 45% DMSO)
1×1.6 ml KCl solution
1×70 µl H5-primer mixture D. Nucleic Acid Detection Components 1×0.9 Generic ECL detection probe (Ruthenium-labelled DNA oligonucleotide Preservative: 5 g/L 2-chloroacetamide)

1×0.7 ml H5-capture probe (Biotinylated-oligonucleotide Preservative: 5 g/L 2-chloroacetamide)

2×1.7 ml Istrument Reference Solution (Ruthenium-labelled paramagnetic beads)

The materials as listed above are intended to be used for 50 test reactions.

Readily available materials not included in the detection kit that will be used in the test reactions are listed as follows:

| Material | Recommended Source |
|---|---|
| 70% (v/v) Ethanol (prepared from 96-100% (v/v) ethanol, ACS quality); use nuclease-free water for dilution | Merck 1.00983 |
| Acetone, analytical grade | SIGMA A4206 |
| Diethylpyrocarbonate for the preparation of RNase-free water | SIGMA D5758 |

Preparation of Reagents

A. Lysis Buffer

Pre-warm Lysis buffer for 30 min at 37° C. before starting the release procedure.

Mix the Lysis buffer vial every 10 min during the incubation to ensure that any crystals have fully dissolved.

Allow Lysis buffer to cool to room temperature.

Protect Lysis buffer from excessive heat or light.

B. Nucleic Acid Isolation Reagents

Bring all reagents to room temperature before use.

Re-use of reagents: If less than 10 samples are being analysed, the remainder of the isolation reagents may be stored at −20° C. for up to two weeks.

1. Wash Buffer

Pre-warm Wash buffer for 30 min at 37° C. before starting the isolation procedure.

Mix the Wash buffer vial every 10-min during the incubation to ensure that any crystals have fully dissolved.

Allow Wash buffer to cool to room temperature.

Protect Wash buffer from excessive heat or light.

C. Nucleic Acid Amplification Reagents

Bring all reagents to room temperature before use.

Re-use of reagents: The reconstituted Reagent spheres and the unused Enzyme solution can be re-used within two weeks provided they have been stored at −70° C. Re-use of all other amplification reagents is possible if the unused portions have been stored at −20° C.

1. Preparation of Reassert Spheres/KCl Solution

Add 80 μl Reagent sphere diluent to the lyophilised Reagent spheres and immediately vortex well. DO NOT centrifuge.

Add 30 μl of KCl solution to the diluted spheres and vortex.

2. Preparation of the Target RNA-Specific Primer Solution

Transfer 110 μl of the Reagent sphere/KCl solution into a fresh test tube and add 10 μl of the 5-primer mixture. Mix well by vortexing. DO NOT centrifuge.

3. Enzyme Solution

Thaw the Enzyme solution at room temperature and mix gently by flicking the tube with fingers. DO NOT vortex any solution containing enzymes. Centrifuge tube contents before use.

D. Nucleic Acid Detection Reagents

Re-use of detection reagents is possible if the unused reagents have been stored at 2-8° C.

1. Capture and Detection Probe

Detection of specific RNA amplicons is carried out with the generic detection probe in the kit in combination with an H5-capture probe previously coupled to paramagnetic beads.

2. H5 RNA Hybridisation Solution

Vortex H5-capture beads until an opaque solution has formed.

For N H5 RNA-specific reactions:

add (N+2)×10 µl H RNA-specific capture beads to a fresh test tube add (N+2)×10 µl generic ECL probe Vortex hybridisation solution before use.

RNA Amplification in Vitro

A. Nucleic Acid Release and Isolation

1. Pre-warm Lysis buffer tubes for 30 and vortex regularly before starting nucleic acid release.
2. Centrifuge Lysis buffer tubes for 30 sec at 10,000×g
3. Add 100 µl target RNA to Lysis buffer tubes and vortex. In Lysis buffer, specimens can be stored:
   indefinitely at −70° C.
   up to 14 days at 2-8° C.
   up to 48 hours at 25° C.
4. Vortex the Silica suspension and add 50 µl to each sample RNA/Lysis buffer tube.
5. Incubate RNA/Lysis buffer/Silica tubes for 10 min at room temperature (vortex tubes every 2 mm to prevent silica from settling to the bottom).
6. Centrifuge RNA/Lysis buffer/Silica tubes for 30 sec at 10,000×g.
7. Carefully remove the supernatant (do not disturb the pellets) and add 1 ml Wash buffer to each tube.
8. Vortex tubes until the pellets have resuspended completely.
9. Centrifuge tubes for 30 sec at 10,000×g.
10. Repeat steps (7) to (9)
    Once with Wash buffer
    Twice with 70% ethanol
    Once with acetone.
11. After the final wash step, carefully remove any residual acetone with a 100 µl pipette.
12. Dry the silica pellets in open test tubes for 10 min at 56° C. on a heating block.
13. When dry, add 50 µl Elution buffer to each test tube.
14. Vortex tubes until the pellets have resuspended completely.
15. Incubate the resuspended silica for 10 min at 56° C. to elute the nucleic acid (vortex the test tubes after 5 min).
16. Centrifuge tubes for 2 min at 10,000×g.
17. Transfer 5 µl of each of the nucleic acid supernatants to a fresh tube and begin the amplification reaction within 1 hr.

B. Nucleic Acid Amplification

1. For each H5 RNA reaction, pipette 5 µl of the nucleic acid extract into a fresh test tube.
2. Add 10 µl of the H5 RNA-specific amplification solution. The amplification solution contains Primers A and B for the detection of non-pathogenic H5 virus.
3. Incubate tubes for 5 mm at 65° C. in a heating block.
4. Cool tubes for 5 min at 41° C. in heating block.
5. Add 5 µl of Enzyme solution and mix well by flicking the test tube with finger.

6. Immediately return test tubes to 41° C. for 10 min.
7. Briefly centrifuge the tubes and incubate them for 90 min at 41° C. in a water bath.
8. Detection of the amplification products may now be performed. As an alternative, the amplification products may be stored at −20° C. for up to 1 month.
9. If the detection result for the presence of non-pathogenic H5 virus is positive, an amplification solution containing Primers A and C for the detection of pathogenic H5 virus may now be applied onto the amplification products by repeating steps 2-8.

C. Nucleic Acid Detection

1. Vortex the hybridisation solutions until opaque. Add 20 μl fit of target RNA hybridisation to each of the hybridisation tubes.
2. For the amplification reactions:
    Add 5 μl H5 RNA amplification reaction.
    Cover the hybridisation tubes with adhesive tape.
    Mix the hybridisation tubes until an opaque solution forms.
3. Use adhesive tape to cover the hybridisation tubes. This is to prevent evaporation and contamination.
4. Incubate hybridisation tubes for 30 min at 41° C.
5. Add 300 μl assay buffer to each hybridisation tube.

The samples are now ready to be detected for the presence of H5 virus by a suitable detection equipment. The detection in this example is preformed on a suitable system equipped with a photomultiplier tube.

The results of H5 virus detection are listed in the follow tables. The results are confirmed by DNA sequencing using a Perkin Elmer ABI 310 Genetic Analyzer.

TABLE 1

Results of the detection for non-pathogenic H5 virus by the detection kit using Primers A and B

| | H5 Subtype Detection | |
|---|---|---|
| Case/sample no. | Detectable Count | Result Classification |
| 258/97 | 4229 | Positive |
| 977/97-2 | 6961 | Positive |
| 1000/97 | 33835 | Positive |
| 1258/97-2 | 2500 | Positive |
| 1258/97-3 | 2400 | Positive |
| 1258/97-4 | 10494 | Positive |
| 1258/97-5 | 3089 | Positive |
| 1258/97-9 | 4883 | Positive |
| 1258/97-10 | Protocol optimization | |
| 437/99-4 | 5165 | Positive |
| 437/99-6 | 22200 | Positive |
| 437/99-8 | 5142 | Positive |
| 437/99-10 | 511 | Positive |
| Negative control 1 | 1 | Negative |
| Negative control 2 | 1 | Negative |
| Negative control 3 | 35 | Negative |

TABLE 2

Results of the detection for pathogenic H5 virus by the detection kit using Primers A and C

| | H5 Pathogenicity Detection | |
|---|---|---|
| Case/sample no. | Detectable Count (×$10^3$) | Result Classification |
| 258/97 | 11800 | Positive |
| 977/97-2 | 5300 | Positive |
| 1000/97 | 23100 | Positive |
| 1258/97-2 | 61800 | Positive |
| 1258/97-3 | 85100 | Positive |
| 1258/97-4 | 68400 | Positive |
| 1258/97-5 | 15800 | Positive |
| 1258/97-9 | 5400 | Positive |
| 1258/97-10 | Protocol optimization | |
| 437/99-4 | 48400 | Positive |
| 437/99-6 | 27100 | Positive |
| 437/99-8 | 21100 | Positive |
| 437/99-10 | 11600 | Positive |
| Negative control 1 | 1 | Negative |
| Negative control 2 | 3 | Negative |
| Negative control 3 | 2 | Negative |

As shown in the above example, it can be realized that the detection kit may be used conveniently in various testing sites including farms. Furthermore, the detection kit is relatively easier to use than existing methods, and may be able to provide the detection results in a shorter time—the detection results may be available within one day if desired. As it is a RNA-based detection system, the specificity and the sensitivity may be enhanced—the detection it is specific to H5 virus, and the concentration of the H5 virus in the sample may no longer be important as the virus will be replicated to a target molecule for detection.

It will be apparent to one skilled in the art that the primers, detection probe, and capture probe may be also useful in the form of RNA molecules. DNA molecules are preferred due to stability reason.

Although the preferred embodiment of this invention has been described in previous paragraphs, it should be apparent to one skilled in the art that modifications and alternative editions of this invention are possible, and such modifications and editions are still within the scope of this invention, which is set forth in the following claims. In addition, the embodiments of this invention shall not be interpreted restrictively by the examples or figures only.

List 1

| Reference No. | Description |
|---|---|
| 10 | nucleic acids in sample |
| 12 | silica |
| 14 | nucleic acids/silica mixture |
| 20 | H5 viral RNA |
| 22 | Primer A |
| 24 | Extended Primer A |
| 26 | Extended Primer A(DNA): H5 viral RNA hybrid |
| 28 | Primer B |
| 30 | double-stranded DNA copy of H5 virus |
| 32 | target RNA molecule |
| 40 | detection probe |
| 41 | signal generator |
| 42 | capture probe |
| 44 | immobilizer |

The invention claimed is:

1. A kit for detecting haemagglutinin gene-containing influenza A subtype H5 virus in a biological sample comprising:
   (i) an isolating agent for isolating RNA molecules of the H5 virus from the biological sample and producing isolated RNA molecules therefrom;
   (ii) a nucleic acid amplifying agent for amplifying the isolated RNA molecules of the H5 virus and producing amplified target molecules for detection, wherein the nucleic acid amplifying agent includes:
      (a) a first purified and isolated DNA molecule consisting of:
         (1) a first DNA sequence consisting of any one of the DNA sequences of SEQ ID NO. 1, SEQ ID NO. 2 and SEQ ID NO. 3; and
         (2) a second DNA sequence encoding a promoter DNA sequence of a RNA polymerase;
         wherein the DNA sequences of SEQ ID NO. 1, SEQ ID NO. 2 and SEQ ID NO. 3 are bindable at regions between 1107 to 1132, 1060 to 1140 and 1040 to 1160, of the haemagglutinin gene, respectively; and
      (b) a second purified and isolated DNA molecule consisting of:
         (1) a third DNA sequence encoding at least a portion of the RNA sequence of the H5 virus and consisting of any one of the DNA sequences of SEQ ID NO. 5, SEQ ID NO. 6, SEQ ID NO. 7, SEQ ID NO. 9, SEQ ID NO. 10, and SEQ ID NO. 11; and
         (2) a fourth DNA sequence encoding a fifth DNA sequence for binding to a detection molecule;
         wherein the DNA sequences of SEQ ID NO. 5, SEQ ID NO. 6, SEQ ID NO.7, SEQ ID NO.9, SEQ ID NO. 10 and SEQ ID NO. 11 are bindable at regions between 914 to 940, 866 to 961, 846 to 981, 1017 to 1042, 970 to 1063 and 950 to 1083, of the haemagglutinin gene, respectively; and
   (iii) a nucleic acid detecting agent for detecting the target molecule; wherein the nucleic acid detecting agent includes the detection molecule.

2. The kit for detecting H5 virus as claimed in claim 1, wherein the kit further comprises a lysis agent for stabilizing nucleic acids in the biological sample.

3. The kit for detecting H5 virus as claimed in claim 1, further comprising an adsorbent for adsorbing nucleic acids.

4. The kit for detecting H5 virus as claimed in claim 1, wherein the target molecule is a RNA molecule.

5. The kit for detecting H5 virus as claimed in claim 1, wherein the RNA polymerase is bacteriophage T7 RNA polymerase.

6. The kit for detecting H5 virus as claimed in claim 1, wherein the DNA sequence encoding the promoter DNA sequence of the RNA polymerase is set forth in SEQ ID NO. 4.

7. The kit for detecting H5 virus as claimed in claim 1, further comprising a reverse transcriptase.

8. The kit for detecting H5 virus as claimed in claim 1, further comprising a RNaseH.

9. The kit for detecting H5 virus as claimed in claim 1, wherein the second purified and isolated DNA molecule or the fifth DNA sequence includes the DNA sequence set forth in SEQ ID NO. 8.

10. The kit for detecting H5 virus as claimed in claim 1, further comprising a detection probe for generating a signal.

11. The kit for detecting H5 virus as claimed in claim 1, further comprising an immobilizer whereby the target molecule can be immobilized when bound to the second purified and isolated DNA molecule.

12. A kit for detecting haemagglutinin gene-containing influenza A subtype H5 virus in a biological sample comprising:
   (i) an isolating agent for isolating RNA molecules of the H5 virus from the biological sample and producing isolated RNA molecules therefrom;
   (ii) a nucleic acid amplifying agent for amplifying the isolated RNA molecules of the H5 virus and producing amplified target molecules for detection, wherein the nucleic acid amplifying agent includes:
      (a) a first purified and isolated DNA molecule consisting of:
         (1) a first DNA sequence consisting of any one of the DNA sequences of SEQ ID NO. 1, SEQ ID NO. 2 and SEQ ID NO. 3; and
         (2) a second DNA sequence encoding a promoter DNA sequence of a RNA polymerase;
         wherein the DNA sequences of SEQ ID NO: 1, SEQ ID NO: 2 and SEQ ID NO: 3 are bindable at regions between 1107 to 1132, 1060 to 1140 and 1040 to 1160, of the haemagglutinin gene, respectively; and
      (b) a second purified and isolated DNA molecule consisting of:
         a third DNA sequence encoding at least a portion of the RNA sequence of the H5 virus and consisting of any one of the DNA sequences of SEQ ID NO. 5, SEQ ID NO. 6, SEQ ID NO. 7, SEQ ID NO.9, SEQ ID NO. 10 and SEQ ID NO. 11;
         wherein the DNA sequences of SEQ ID NO. 5, SEQ ID NO. 6, SEQ ID NO. 7, SEQ ID NO. 9, SEQ ID NO. 10 and SEQ ID NO. 11 are bindable at regions between 914 to 940, 866 to 961, 846 to 981, 1017 to 1042, 970 to 1063 and 950 to 1083 of the haemagglutinin gene, respectively; and (iii) a nucleic acid detecting agent for detecting the target molecule; wherein the nucleic acid detecting agent includes a detection molecule having a nucleic acid sequence encoding a portion of H5 viral RNA sequence that is complementary to that encoded in the target RNA molecule and a signal generator.

13. The kit for detecting H5 virus as claimed in claim 12, wherein the nucleic acid detection agent includes a third purified and isolated DNA molecule including (i) a DNA sequence encoding SEQ ID NO. 12, SEQ ID NO. 13 or SEQ ID NO. 14, and (ii) an immobilizer, such that the target molecule is immobilized when bound to the second purified and isolated DNA molecule.

14. The kit for detecting H5 virus as claimed in claim 12, further comprising a capture molecule for capturing target molecules such that undesired molecules other than the target molecules can be removed.

* * * * *